(12) United States Patent
Scheer et al.

(10) Patent No.: US 7,169,753 B2
(45) Date of Patent: Jan. 30, 2007

(54) CHLOROPHYLL AND BACTERIOCHLOROPHYLL ESTERS, THEIR PREPARATION AND PHARMACEUTICAL COMPOSITIONS COMPRISING THEM

(75) Inventors: Hugo Scheer, Blonhofen (DE); Nina Kammhuber, Munich (DE); Avigdor Scherz, Rehovot (IL); Alexander Brandis, Rehovot (IL); Yoram Salomon, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 390 days.

(21) Appl. No.: 10/148,552

(22) PCT Filed: Dec. 1, 2000

(86) PCT No.: PCT/IL00/00811

§ 371 (c)(1),
(2), (4) Date: Nov. 6, 2002

(87) PCT Pub. No.: WO01/40232

PCT Pub. Date: Jun. 7, 2001

(65) Prior Publication Data

US 2003/0148926 A1    Aug. 7, 2003

(30) Foreign Application Priority Data

Dec. 1, 1999 (IL) .................... 133253

(51) Int. Cl.
*A61K 38/00* (2006.01)
(52) U.S. Cl. ........................ 514/6
(58) Field of Classification Search ........ 514/6
See application file for complete search history.

(56) References Cited

U.S. PATENT DOCUMENTS 5,171,741 A    12/1992  Dougherty 6,333,319 B1 * 12/2001 Scherz et al. ............... 514/185

FOREIGN PATENT DOCUMENTS

| DE | 41 21 867 A1 | 1/1993 |
| EP | 0 584 552 A2 | 2/1994 |
| WO | WO 90/12573 | 11/1990 |
| WO | WO 97/19081 | * 5/1997 |

OTHER PUBLICATIONS

S. Shinoda et al. "Transesterification of the Alph-Keto Ester in Methyl Pheophoribide -a", Tetrahedron Letters Jul. 1996, 4945-4948, vol. 37, No. 28.
X. Jiang et al. "Synthesis of Nucleoside Adducts of Porphyrins and Chlorophyll Derivatives", Tetrahedron Letters Jan. 1995, 365-368, vol. 36 No. 3.
E. Zass et al. "Der Einbau von Magnesium in Liganden der Chlorophyll-Reihe mit (2. 6-Di-tbutyl-4-methylphenoxy) magnesiumjodid", Helvetica Chimica ACTA Nov. 1980, 1048-1067, vol. 63, No. 4.
H. Tamiaki et a, "Aggregation of Synthetic Zinc Chlorins with Several Esterified Alkyl Chains as Models of Bacteriochlorophyll-c Homologs", Tetrahedron Jun. 1996, 12421-12432 vol. 52, No. 38.
T. J. Michalski et al, "Enzyme-Catalyzed Organic Syntheses: Transesterification Reactions fo Chlorophyll a, Bacteriochlorophyl a, and Derivatives with Chlorophyllase" J. Am. Chem. Soc. Dec. 1987. 5888-5891, vol. 110.

* cited by examiner

Primary Examiner—Cecilia J. Tsang
Assistant Examiner—Maury Audet
(74) Attorney, Agent, or Firm—Browdy and Neimark, PLLC (57) ABSTRACT

Novel $C-13^2-COXR_1$, $C-17^2-COXR_2$ and $C-13^2-COXR_1$, $C-17^2-COXR_1$ derivatives of chlorophyll and bacteriochlorophyll compounds are provided wherein X is O, S or N and $R_1$ and $R_2$, the same or different, may be an optionally substituted hydrocarbyl, amino acid, peptide, protein or saccharide radical. The compounds are for use in photodynamic therapy (PDT), for diagnosis of tumors, and for killing cells and infectious agents such as bacteria and virus, both in biological products and in living tissues.

16 Claims, 3 Drawing Sheets

CHLOROPHYLL AND BACTERIOCHLOROPHYLL ESTERS, THEIR PREPARATION AND PHARMACEUTICAL COMPOSITIONS COMPRISING THEM

FIELD OF THE INVENTION

The present invention relates to novel derivatives of chlorophyll and bacteriochlorophyll, their preparation and their use in methods of in vivo photodynamic therapy (PDT) and diagnosis and in vitro photodynamic killing of viruses and microorganisms.

DEFINITIONS AND ABBREVIATIONS

BChl=bacteriochlorophyll a (the Mg-containing 7,8,17,18-tetrahydroporphyrin of the formula (a) in Scheme A hereinafter wherein M is Mg, and having a phytyl or geranylgeranyl group at position $17^3$, a $COOCH_3$ group at position $13^2$, an H atom at position $13^2$, an acetyl group at position 3, and an ethyl at position 8).

BChl derivative=a derivative of BChl with modifications in the macrocycle, in the central metal atom and/or in the periphery.

BChlide: bacteriochlorophyllide a (the $C-17^2$-free carboxylic acid derived from BChl).

BPhe=bacteriopheophytin a (BChl in which the central Mg is replaced by two H atoms).

BPheid: bacteriopheophorbide a (the $C-17^2$-free carboxylic acid derived from BPhe).

Chl (b)=chlorophyll a (b) (the Mg-containing 17,18-dihydroporphyrin of the formula (b) in Scheme A hereinafter wherein M is Mg, and having a phytyl group at position $17^3$, a $COOCH_3$ group at position $13^2$, an H atom at position $13^2$, a vinyl group at position 3, a double bond at positions 7–8, and either a methyl at position 7 and an ethyl at position 8 (Chl a) or a formyl group at position 7 and an ethyl at position 8 (Chl b)).

Chlide: chlorophyllide a (the $C-17^2$-free carboxylic acid derived from Chl).

DMF: dimethylformamide; ESI: electro spray ionization; et: ethyl; gg: geranylgeranyl; glc: glucose; HPLC: high pressure liquid chromatography; FITC: fluorescein isothiocyanate.

[M]-BChl=BChl derivative in which the central Mg atom has been replaced by a metal M as defined hereinafter.

me: methyl; MS: mass spectroscopy; NMR: nuclear magnetic resonance; NtBoc-ser: N-tert-butyloxycarbonyl-seryl; PDT: photodynamic therapy.

Phe=pheophytin a (Chl in which the central Mg is replaced by two H atoms).

Pheid: pheophorbide a (the $C-17^2$-free carboxylic acid derived from Phe);

pr: 1-propyl; SDP: site-directed photodynamic therapy, ser: seryl, serine; tbb=para-tert-butyl-benzyl; THF: tetrahydrofuran; $Ti(OEt)_4$: tetraethyl-ortho-titanate.

Throughout the specification, the nomenclature and numbering of the (bacterio)chlorophyll structures used is according to IUPAC (see Scheme A hereinafter). Using this nomenclature, the native (bacterio)chlorophylls carry two carboxylic ester groups at positions $C-13^2$ and $C-17^2$ that are esterified at positions $C-13^3$ and $C-17^3$. In the nomenclature and abbreviations used in the examples, the esterifying residue at $C-13^3$ appears first, followed by the central metal atom, if not Mg, and then the tetrapyrrole name followed by the $C-17^3$ ester residue. For example, the compound of Example 1 hereinafter is designated $13^3$-tert-butyl-benzyl-Pd-bacteriopheophorbide a-$17^3$-methyl ester (abbreviated as tbb-Pd-BPheid-me).

BACKGROUND OF THE INVENTION

Chlorophylls and bacteriochlorophylls, the ubiquitous pigments of photosynthesis, have been studied intensively in order to understand their photophysics and photochemistry (Scheer, 1991). Together with the more readily available but spectroscopically less informative porphyrins, they have also been used to gain a more general insight into energy and electron transfer, the mutual interactions of large aromatic molecules with central metals, and of the central metals with extra ligands.

Photosensitizers are of interest for utilization in photodynamic therapy (PDT) of tumors. This technique utilizes a combination of a non-toxic drug that absorbs light at a suitable wavelength with non-hazardous photosensitizing irradiation of the patient following administration of the drug.

Porphyrins have been shown to accumulate in tumor tissue and, upon irradiation of the tumor tissue, to absorb light in situ, providing a mean to detect tumors by location of the fluorescence. A crude derivative of hematoporphyrin, known as hematoporphyrin derivative or HPD, has been proposed both for detection and for photodynamic therapy of tumors. A form of HPD said to be more effective comprises a portion of HPD having an aggregate weight over 10 Kda and is the subject of U.S. Pat. No. 4,649,151. HPD or its active components have been described in U.S. Pat. No. 4,753,958 for topical treatment of skin diseases, and in Matthews et al., 1988, for sterilization of biological samples containing infectious organisms such as bacteria and virus. A mixture known as hematoporphyrin derivative (HPD) containing a high proportion of ether-linked hematoporphyrin (HP) oligomers is commercially available (Photofrin II, Quarda Logic Technologies Inc., Vancouver, BC, Canada).

In order to optimize the performance of the porphyrin drugs in therapeutics and diagnostics, several porphyrin derivatives have been proposed in which, for example, there is a central metal atom complexed to the four pyrrole rings, and/or the peripheral substituents of the pyrrole rings are modified and/or the macrocycle is dihydrogenated to Chl derivatives (chlorins) or tetrahydrogenated to BChl derivatives (bacteriochlorins).

Chlorophyll and bacteriochlorophyll derivatives have superior properties in comparison to porphyrins, but are less readily available and more difficult to handle. The potential of chlorophyll derivatives (Spikes and Bommer, 1991) and of bacteriochlorophyll derivatives (Beems et al., 1987; Dougherty, 1992; Fiedor et al., 1993; Kessel et al., 1993; Moser, 1998; Pandey et al., 1994; Tregub et al., 1993) for the diagnosis and therapy of cancer, has been studied. Due to their intense absorption in favorable spectral regions (650–850 nm) and their ready degradation after treatment, chlorophyll and bacteriochlorophyll derivatives have been identified as excellent sensitizers for PDT of tumors.

Complexes of cyclic tetrapyrroles with metals other than Mg were studied in the porphyrin and 17,18-dihydroporphyrin series to understand their spectroscopic and redox properties (Hynninen, 1991). Bacteriochlorophylls are of potential advantage compared to the chlorophylls because they show intense near-infrared bands, i.e. at considerably longer wavelengths than chlorophyll derivatives.

PCT International Application Publication No. WO 90/12573 to Dougherty describes derivatives of bacteriochlorophyll-a or -b or of the corresponding bacteriochlorins devoid of the central metal atom or in which the central metal atom may be a non-paramagnetic metal selected from $Mg^{2+}$, $Sn^{2+}$ and $Zn^{2+}$, and the C-$17^2$-carboxyl group is esterified with a saturated or unsaturated hydrocarbyl residue of 8–25C, for the manufacture of a composition for use in a method to effect the destruction or impairment of undesired target biological substrates, which method comprises photosensitizing said substrate with an effective amount of said derivative, followed by irradiation of the target substrate with radiation in a wavelength band absorbed by said derivative for a time effective to impair or destroy the substrate. In addition, the compounds are said to be useful in photodynamic therapy and diagnostics. It is to be noted that although $Sn^{2+}$ and $Zn^{2+}$ complexes of bacteriochlorophyll-a or -b are claimed, these metal derivatives have not been exemplified nor was any method for their preparation described in the specification of said patent application WO 90/12573.

Under normal delivery conditions, i.e. in the presence of oxygen at room temperature and under normal light conditions, the BChl moieties are labile and have somewhat lower quantum yields for triplet state formation, when compared with, e.g., hematoporphyrin derivative (HPD). However, their possible initiation of biological redox reactions, favorable spectral characteristics and their ready degradation in vivo result in the potential superiority of bacteriochlorophylls over other compounds, e.g. porphyrins and chlorophylls, for PDT therapy and diagnostics and for killing of cells, viruses and bacteria in samples and in living tissue. Chemical modification of bacteriochlorophylls is expected to further improve their properties, but this has been very limited due to lack of suitable methods for the preparation of such modified bacteriochlorophylls (Hynninen, 1991).

European Patent Application published under No. 0584552 of the same applicant of the present application describes new conjugates of chlorophylls and bacteriochlorophylls at the C-$17^3$ position with amino acids, peptides and proteins for use in PDT therapy and diagnostics. The amino acid, peptide or protein residue is linked directly or via a spacer to the C-$17^2$-carboxyl group of the chlorophyll or bacteriochlorophyll molecule. These conjugates are prepared by methods which are mild enough to retain the acid-labile central Mg atom.

The C-$13^2$-carbomethoxy group of chlorophylls and bacteriochlorophylls is biosynthetically derived from the C-13 propionic acid side chain and part of the reactive β-ketoester system present in most chlorophylls at the isocyclic ring. However, unlike the C-17 propionic ester side chain, no methods have been available for either chemical or enzymatic transesterification at the C-$13^3$ position. The only reaction previously known for this group was its cleavage, leading to the $13^2$-demethoxycarbonyl- or pyro-chlorophylls. German Patent Application No. DE 4121876 and PCT Publication No. WO 97/19081, both assigned to the present applicant, propose bacteriochlorophyll derivatives with modified ester residues at positions $13^3$ and $17^3$. However, these patent applications describe only bacteriochlorophyll derivatives with native methyl ester residues at position $13^3$ and no methods for the preparation of other esters at position $13^3$ were described therein.

It would be desirable to prepare new chlorophyll and bacteriochlorophyll derivatives for use in PDT, in order to maintain or even improve the favorable optical and physiological properties of Chls and BCbls while optimizing their photosensitizing potential as well as improving their chemical stability and optimizing their physiological lifetimes.

SUMMARY OF THE INVENTION

It has now been found in accordance with the present invention that novel C-$13^2$ esters, thioesters and amides and C-$13^3$/C-$17^3$ diesters, dithioesters and diamides of chlorophylls and bacteriochlorophylls can be obtained by selectively transesterifying, thioesterifying or amidating the C-$13^2$-carbomethoxy group of chlorophyll and bacteriochlorophyll derivatives either alone or together with the C-17 propionic acid side chain under anhydrous and anaerobic conditions in the presence of excess alcohol, mercaptan or amine and using tetraethyl-o-titanate as catalyst. This procedure is mild enough to allow for the modification, e.g. transesterification, of acid-labile pigments like the native Mg-containing chlorophylls.

The present invention thus relates to novel chlorophyll and bacteriochlorophyll derivatives of the general formula I:

and pyro-derivatives thereof wherein the radical $COXR_1$ at position $13^2$ is absent, wherein X is O, S or NH;

M is a central metal atom or represents two H atoms;

$R_3$ and $R_5$ are each, independently, acetyl, vinyl, ethyl, 1-hydroxyethyl or an ether or ester of said 1-hydroxyethyl radical;

$R_4$ is methyl or formyl;

the dotted line at positions 7–8 represents an optional double bond; and $R_1$ and $R_2$, the same or different, are selected from the group consisting of:

(i) a $C_1$–$C_{25}$ hydrocarbyl radical that may be straight or branched, saturated or unsaturated, optionally substituted by one or more radicals selected from halogen, oxo (=O), OH, CHO, COOH or $NH_2$, or interrupted by one or more heteroatoms selected from O, S and NH, or by carbocyclic or heterocyclic moieties;

(ii) a residue of an amino acid, an oligopeptide or a polypeptide containing a hydroxy group or of a derivative thereof selected from the group consisting of esters and N-protected derivatives, wherein said hydroxylated amino acid or derivative thereof is linked to the COO⁻ residue of the Chl or BChl derivative through said hydroxy group;

(iii) a residue of a peptide as defined in (ii) linked to the COO⁻ residue via a $C_1$–$C_{25}$ hydrocarbyl as defined in (i)

wherein said $C_1$–$C_{25}$ saturated or unsaturated hydrocarbyl residue optionally substituted by one or more radicals selected from halogen, oxo (=O), OH, CHO, COOH or $NH_2$, or such a residue interrupted by one or more heteroatoms selected from O, S and NH, or by a phenyl ring is further substituted by an end functional group selected from OH, COOH, or $NH_2$;

(iv) a residue of a cell- or tissue-specific ligand selected from an oligo-peptide and a protein directly linked to the $COO^-$ residue or via a $C_1$–$C_{25}$ hydrocarbyl as defined in (i) wherein said $C_1$–$C_{25}$ saturated or unsaturated hydrocarbyl residue optionally substituted by one or more radicals selected from halogen, oxo (=O), OH, CHO, COOH or $NH_2$, or such a residue interrupted by one or more heteroatoms selected from O, S and NH, or by a phenyl ring, is further substituted by an end functional group selected from OH, COOH, or $NH_2$; and (v) a residue of a mono-, oligo- or polysaccharide or from polyoxyethylene directly linked to the $COO^-$ residue or via a $C_1$–$C_{25}$ hydrocarbyl as defined in (i) wherein said $C_1$–$C_{25}$ saturated or unsaturated hydrocarbyl residue optionally substituted by one or more radicals selected from halogen, oxo (=O), OH, CHO, COOH or $NH_2$, or such a residue interrupted by one or more heteroatoms selected from O, S and NH, or by a phenyl ring, is further substituted by an end functional group selected from OH, COOH, or $NH_2$;

with the proviso that $R_1$ is not methyl when $R_2$ is ethyl, phytyl, geranylgeranyl or the residue of an amino acid, a peptide or a protein or of derivatives thereof.

The compounds of formula I wherein $R_3$ is vinyl, $R_4$ is methyl or formyl, $R_5$ is ethyl and the dotted line at positions 7–8 represents a double bond, are the derivatives of chlorophyll a and b, respectively. The compounds of formula I wherein $R_3$ is acetyl, $R_4$ is methyl, $R_5$ is ethyl and the positions 7–8 are hydrogenated, are the derivatives of bacteriochlorophyll a.

The central metal atom M in the compound of formula I may be absent, may be the native Mg atom of the natural chlorophyll and bacteriochlorophyll pigments, or it may be a divalent metal selected from the group consisting of Pd, Co, Ni, Cu, Zn, Hg, Er, Ti, Eu, Sn and Mn.

The present invention also relates to a new transesterification process for the preparation of the synthetic chlorophyll and bacteriochlorophyll derivatives of the general formula I above, wherein X is O, said process comprising the steps of:

(a) reacting an appropriate (bacterio)chlorophyll, metal-(bacterio)chlorophyll or (bacterio)pheophytin derivative carrying at position $C-13^2$ a $COOCH_3$ group and at position $C-17^2$ a $COOR_2$ group, with an alcohol $R_1OH$, wherein $R_1$ and $R_2$ are as defined above, with the proviso that $R_1$ is not methyl, in the presence of tetraethyl-ortho-titanate, wherein the reaction is performed either in a solvent such as peroxide-free tetrahydrofuran (THF) or dimethylformamide (DMF), in which case the $C-13^2$-$COOR_1$, $C-17^2$-$COOR_2$ diester is preferentially obtained, or the alcohol $R_1OH$ is used in large excess and serves as the solvent, in which case the $C-13^2$-$COOR_1$, $C-17^2$-$COOR_1$ diester is obtained; and (b) separating the desired products from the reaction mixture.

For the preparation of compounds of formula I wherein X is S, the corresponding mercaptans of the formula $R_1SH$ are used, and for the compounds wherein X is N, the corresponding amines $R_1NH_2$ are used.

The procedures of the invention can be used in combination with other known procedures for the modification of the molecule, for example conjugation at the $C-17^3$ position as described in EP 0584552, modifications at the periphery of the molecule and/or transmetalation, for example as described in WO 97/19081. Preferably, demetalation or exchange of the central metal atom is carried out before transesterification.

The new chlorophyll and bacteriochlorophyll compounds of the invention are for use as photosensitizers as therapeutic and diagnostic agents for example against cancer and age-related macular degeneration, and for killing cells, viruses and bacteria in samples and living tissues as well known in the art of PDT and other photosensitizer applications.

DETAILED DESCRIPTION OF THE INVENTION

The present invention relates to new $C-13^2$-$COXR_1$, $C-17^2$-$COXR_2$ and $C-13^2$-$COXR_1$, $C-17^2$-$COXR_1$ derivatives of chlorophyll and bacteriochlorophyll compounds wherein X is O, S or N.

In one embodiment of the invention, $R_1$ and $R_2$ are identical; in another embodiment, they are different.

In one embodiment of the present invention, $R_1$ and $R_2$ may be a hydrocarbyl radical. As used herein, "hydrocarbyl" means any straight or branched, saturated or unsaturated, including aromatic, hydrocarbyl radicals, preferably of 1–25 carbon atoms, such as alkyl, preferably of 1–4 carbon atoms, e.g. methyl, ethyl, propyl, butyl or alkenyl, alkynyl, cycloalkyl, aryl such as phenyl or an aralkyl group such as benzyl or substituted benzyl, e.g. tert-butylbenzyl. When $R_1$ and $R_2$ are different, $R_1$ is preferably methyl, the radical present in natural Chl and BChl compounds, and $R_2$ is preferably ethyl or a radical derived from natural Chl and Bchl compounds, e.g. geranylgeranyl (2,6-dimethyl-2,6-octadienyl) or phytyl (2,6,10,14-tetramethylhexadec-14-en-16-yl). When $R_1$ and $R_2$ are different $R_1$ and $R_2$ may also be a hydrocarbon chain substituted by one or more radicals selected from halogen such as F, Br, Cl and I, or OH, oxo (=O), CHO, COOH or $NH_2$, or such an optionally substituted hydrocarbyl chain interrupted by O, S or NH, preferably O, e.g. $R_1$ or $R_2$ is an oligooxyethyleneglycol residue of 4 to 10 carbon atoms, preferably pentaoxyethyleneglycol, or by carbocyclic, e.g. phenyl, or heterocyclic, e.g. pyridyl, moieties.

In another embodiment, $R_1$ and $R_2$ may be the residue of an amino acid or of a peptide (oligo or polypeptide) containing a hydroxy group, such as serine, threonine and tyrosine, or peptides containing them, or a derivative of said amino acid or peptide selected from esters, e.g. alkyl esters, and N-protected derivatives wherein the N-protecting group is for example tert-butyloxy, carbobenzoxy or trityl, and said hydroxylated amino acid or peptide or derivative thereof is linked to the COO— group of the Chl or BChl derivative through its hydroxy group. Examples of such amino acid derivatives are serine methyl ester, N-tert-butyloxycarbonyl-serine, N-trityl-serine methyl ester, tyrosine methyl ester, and N-tert-butoxy-tyrosine methyl ester, and an example of such a peptide is N-carbobenzoxy-seryl serine methyl ester, all of them prepared as described in EP 0584552. In a preferred embodiment, the Chl or BChl derivative is esterified with L-serine or with N-tert-butyloxycarbonyl-serine.

In a further embodiment, $R_1$ and $R_2$ may be the residue of a peptide (oligo or polypeptide) linked to the Chl or BChl through a $C_1$–$C_{25}$ hydrocarbyl radical as defined above, in which case the hydrocarbyl radical serves as a spacer for said peptide or polypeptide/protein and has an end functional group selected from OH, COOH and $NH_2$, through which end functional group the peptide or protein is linked by an ester or amide bond.

In another further embodiment, $R_1$ and $R_2$ may be the residue of a cell-specific or tissue-specific ligand selected from peptides and proteins, which are exemplified by, but not limited to, hormone peptides, e.g. melanocyte-stimulating hormones (melanotropins), and antibodies, e.g. immunoglobulins and tumor-specific antibodies. Also in this case, the peptide or protein may be linked to the Chl or BChl through a $C_1$–$C_{25}$ hydrocarbyl radical as defined above, in which case the hydrocarbyl radical serves as a spacer for said peptide or polypeptide/protein and has an end functional group selected from OH, COOH and $NH_2$, through which end functional group the peptide or protein is linked by an ester or amide bond.

In still a further embodiment, $R_1$ and $R_2$ may be the residue of a mono-, oligo- or polysaccharide directly linked to the $COO^-$ of the Chl or BChl molecule or through a $C_1$–$C_{25}$ hydrocarbyl radical as defined above. In a preferred embodiment, the monosaccharide is glucosamine.

The invention further relates to pyroderivatives of the Chl and BChl compounds of the formulas IV and V in Scheme B herein in which the carbomethoxy ($COOCH_3$) group of natural Chl and BChl compounds is replaced by a H atom. These pyroderivatives are obtained from the $C-13^2$-$COOR_1$, $C-17^2$-$COOR_2$ and $C-13^2$-$COOR_1$, $C-17^2$-$COOR_1$ diesters of the invention by pyrolysis with pyridine (see Scheme B).

For the preparation of the esters of the invention (compounds wherein X is O), transesterification at the $C-13^3$ position only is preferentially carried out by reacting a Chl or BChl $C-17^3$, $C-13^3$ diester derivative carrying a native carbomethoxy group at the $C13^3$ position with the desired alcohol $R_1OH$, wherein $R_1$ is not methyl, in the presence of tetraethyl-ortho-titanate, wherein the reaction is performed in an aprotic solvent such as peroxide-free tetrahydrofuran (THF) or dimethylformamide (DMF). Several esters were prepared by this method as described below with ethanol, tert-butyl-benzyl alcohol, propanol, tert-butyloxycarbonyl-serine and serine.

In another embodiment, transesterification at both $C-13^3$ and $C-17^3$ positions is performed simultaneously with an alcohol $R_1OH$. The synthesis follows the above procedure, but the alcohol is used as a solvent[1]. Several esters were prepared by this method as described below including tbb, Pr, NtBoc-Ser, and ser esters. The reaction time for the para-tert-butyl-benzyl alcohol and for n-propanol were 48 and 12 h, respectively.

[1] Not applicable for NtBoc-ser, which is a solid.

The type of alcohol and the temperature determine whether esterification will occur more at the $C-13^3$ position or at both the $C-17^3$ and $C-13^3$ positions. Large $R_1OH$ alcohos will preferentially esterify the $C-13^3$ position while small alcohols will esterify both the $C-17^3$ and $C-13^3$ positions.

The preferable solvent according to the invention is THF. DMF is used when the alcohol is insoluble in THF. The reaction mixture may be kept at 75° C. for several days such as in the cases of 1-propanol, para-tert-butyl-benzyl alcohol and N-tBoc-serine.

The separation of the products from the reaction mixture is carried out by standard methods, for example by addition of diethyl ether and water until phase separation occurs, three-fold extraction of the aqueous phase with ether, drying of the combined organic phases with NaCl, evaporation of the solvent in vacuum, removal of the excess alcohol in high vacuum ($<10^{-3}$ Pa), and recovery of the desired, transesterified Chl or BChl derivative by HPLC or column chromatography.

The transesterified Chl and BChl, esters of the invention can be further treated with pyridine at elevated temperature to cleave off the $C-13^2$ carbomethoxy residue and form the pyro-derivatives of formulas IV and V in Scheme B herein. The pigments of formula IV can be further transesterified, thiolated or amidated at position $17^3$.

The Chl and BChl derivatives obtained by both procedures can be used themselves as sensitizers according to the invention or they can be serve as a bridge/spacer to link other suitable molecules to the Chl/BChl macrocycle When an ester is desired and the desired peptide or protein to be attached to one of the positions is devoid of an hydroxyl-containing amino acid residue, the Chl or Bchl macrocycle may first be linked to a serine or any other hydroxyl-containing residue, or with a derivative thereof, by transesterification of the native compounds or by esterification of the corresponding free acids (Chlide or Bchlide), and the peptide or protein is then linked to the macrocycle through this amino acid residue.

Compounds of formula I wherein X is NH at one of the $C-13^3$ or $C-17^3$ positions, may be obtained by catalytic condensation of a Chlide or Bchlide derivative with a compound $R_1$—$NH_2$, e.g. an amine or the terminal amino group of a peptide or protein, in the presence of TBTU in DMF at pH 8–9. One particular product is the amide conjugate of Pd-BPhlide with N-glucosamine.

When a Chlide or Bchlide derivative is reacted with a peptide or protein comprising amino acid moieties containing hydroxyl, mercapto and/or amino radicals, it may not always be clear whether the conjugation will be through an O or an NH group, but all such conjugates are encompassed by the present invention, independent of the identification of their structure.

For preparation of metal-substituted Chl and Bchl derivatives, the native Mg central atom is replaced by the desired metal M prior to conjugation of the pigment to the amino acid or cell-specific ligand. The substitution of the central Mg atom in chlorophyll and its derivatives with Pd, Er, Cu, Ni, Zn, V, Co, Sn, Hg and other divalent metals is carried out by standard procedures, e.g., treating the corresponding pheophytin with a salt of the desired metal, e.g. Zn acetate or Cu acetate in absolute ethanol at ambient temperature (Hambright, 1975; Hynninen, 1991). In the case of bacteriochlorophyll and its derivatives, the central Mg atom can be substituted by Zn, Cu or Pd by a similar procedure involving treatment with Zn, Cu or Pd acetate under argon at elevated temperatures as described in WO 97/19081.

When $R_1$ is a substituted hydrocarbyl, it may contain an end functional group through which it may be attached to other desired residues, for example, an ester group is formed by reaction of either the terminal carboxyl group of $R_1$ with an hydroxyl group of another compound such as an amino acid or a saccharide or of the terminal hydroxyl group of $R_1$ with a carboxyl group of said another compound; an amide group is formed by reaction of the terminal carboxyl group of $R_1$ with an amino group of another compound such as an amino acid, or of the terminal amino group of $R_1$ a with a carboxyl group of another compound such as an amino acid.

The new esters, amides and thioesters of the invention have the same optical absorption and photophysical characteristics as the respective Chls and Bchls. Therefore, once residing within the treated tissue, the new Chl and Bchl esters are expected to be efficient photodynamic agents. They can thus be useful as photosensitizers as therapeutic and diagnostic agents, and for killing cells, viruses and bacteria in samples and living tissues, as well known in the art for HPD and other photosensitizers. These compounds are useful, for example, in sensitizing neoplastic cells or other abnormal tissue to destruction by irradiation either in vivo or ex vivo using light of appropriate wavelenght. It is believed that the energy of photoactivation is transferred to endogenous oxygen to convert it to singlet oxygen, which singlet oxygen is considered to be responsible for the cytotoxic effect. In addition, the photoactivated forms of the (bacterio)chlorophylls fluoresce, which fluorescence can aid in localizing tumors or other sites to which the (bacterio) chlorophylls are administered.

Examples of indications, known in the art, that can be treated with the new (bacterio)chlorophyll derivatives of the invention, include destruction of tumor tissue in solid tumors, dissolution of plaques in blood vessels (see, e.g., U.S. Pat. No. 4,512,762),; treatment of topical conditions such as acne, athlete's foot, warts, papilloma, and psoriasis, and treatment of biological products (such as blood for transfusion) for infectious agents.

The (bacterio)chlorophyll derivatives of the present invention are formulated into final pharmaceutical compositions for administration to the patient or applied to an in vitro target using techniques well-known in the art, for example, as summarized in Remington's Pharmaceutical Sciences, Mack Publishing Co., Easton, Penn., latest edition. The compositions can be administered systemically, in particular by injection, or can be used topically.

For diagnosis, the (bacterio)chlorophyll derivatives may be used alone or may be labeled with a radioisotope or other detecting means as known in the art.

The amount of (bacterio)chlorophyll derivative to be administered will be according to the experience accumulated with other porphyrins used in PDT, and will vary depending on the choice of the derivative used as active ingredient, the condition to be treated, the mode of administration, the age and condition of the patient, and the judgement of the physician.

The wavelenght of irradiating light is preferably chosen to match the maximum absorbance of the (bacterio)chlorophyll photosensitizer. The suitable wavelenght for any of the compounds can readily be determined from its absorption spectrum.

In addition to in vivo use, the (bacterio)chlorophyll derivatives of the invention can be used in the treatment of materials in vitro to kill harmful viruses or infectious agents, such as harmful bacteria. For example, blood and blood plasma to be used for future transfusion can be treated with a compound of the invention and irradiated to effect sterilization.

The conjugation of proteins, e.g., hormones, growth factors or their derivatives and antibodies, and of cell nutrients, e.g. tyrosine, to the Chl and Bchl moiety is meant to increase their retention in tumor and treated sites. Increasing the red shift allows for a greater depth of penetration while keeping the ubiquity of the natural system. Replacement of the Mg by other metals is meant to optimize the intrinsic and metabolic stability of the Chl or Bchl moiety and its intersystem crossing to the excited triplet state, and also opens the possibility for new diagnostic procedures.

Tumor-specific antibodies will preferentially target the Chl and Bchl moieties to the tumor or treated site, while hormones and cell nutrients may also be taken up by the normal non-transformed counterparts. However, the cells selected as targets to hormones and cell nutrients, such as melanocytes, are scattered among other cells under normal conditions and when transformed into malignant cells, cluster into solid tumors. As a result, the concentration of the photosensitizer in the malignant tissue is expected to increase dramatically relative to its concentration in the normal tissue, where cells are more dispersed, assuring amplification of the PDT effect in the tumor site. This enables effective use of light doses, lower than the damaging threshold of the normal tissue, thus reducing the need for spatially well-defined irradiation. In addition, having very strong fluorescence, the site-directed Chl or Bchl can be used for fluorescence labeling of the tumor site(s) or other targets.

Melanoma tumors are suitable for treatment with the new Chl and Bchl photosensitizers of the invention for several reasons: (a) at early stages (non-metastatic), malignant melanoma and other skin tumors are very accessible to PDT; (b) photodynamic therapy using green light as well as conventional chemotherapy and radiotherapy have failed so far in melanoma treatment; (c) there exist, however, several melanoma specific ligands that can target the photosensitizing moiety into the tumor site, and (d) the use of the long wavelength excitable Chl and Bchl moieties is expected to overcome the shortcomings of the conventional photosensitizers, which due to melanin absorption are screened.

Melanoma tumors evolve from carcinogenic transformation (including UV-induced mutagenesis) of melanocytes. Normal melanocytes comprise a few percent of the normal human skin cell population and are normally found in the basal cell layer between the epidermis nad the dermis where each of them is surrounded by 30–40 keratinocytes and one Langerhans cell. PDT faces particular difficult challenge with melanoma tumors since the melanoma tumor cells may contain the insoluble black eumelanins (poly-5,6-indole quinones), which have a broad absorption band around 540 nm and therefore compete with any photosensitizer for the radiation at wavelengths shorter than 650 nm. In addition, the melanin molecules can quench those oxygen radicals that have been formed and thereby prevent the intoxication of vital cell organelles. Consequently, PDT of melanotic melanomas with the commonly used HPD is not very promising. However, having their maximum optical absorption at wavelength above 650 nm, excited Chls and Bchls and their synthetic derivatives should not be shaded by the melanin. Furthermore, melanoma tumor cells (i.e. transformed melanocytes) consume considerable amounts of tyrosine during the synthesis of melanin, have high affinity to melanotropins (the pituitary α-, β-, and γ-melanocyte stimulating hormones (MSH)) and to several known antibodies. Therefore, they can be a good target to tyrosine-, melanocortin-, or antibody-conjugates of Chls and Bchls, provided that the conjugation does not strongly affect ligand recognition by the cell receptors. Since the concentration of the melanocytes increases by a factor of nearly 40 in the melanoma sites (relative to normal skin tissue), the photodynamic effect is expected to increase drastically.

The present invention thus provides pharmaceutical compositions comprising a Chl or Bchl derivatives of the invention for photodynamic therapy of several types of cancer, including brain, ovarian, breast and tumors and skin, lung, esophagus and bladder cancers and other hormone-sensitive tumors.

In one embodiment, the invention relates to photodynamic treatments of malignant melanoma. The photodynamic effect of the compounds is monitored on melanoma cells in tumors and cell cultures. Examples of derivatives that can be used for this purpose are conjugates of Chl or Bchl derivatives with α-melanotropin, linked to the pigment moiety either via its serine, tyrosine or lysine residues or through the terminal amino group.

The pharmaceutical compositions of the invention will be administered to the patient by standard procedures used in PDT. The amount of compound to be administered and the route of administration will be determined according to the kind of tumor, stage of the disease, age and health conditions of the patient, but will be much lower than currently used dosage of Photofrin II of about 20–40 mg HPD/kg body weight. The preferable routes of administration are intravenous or direct injection into the solid tumor of the aqueous solution of the active compound comprising conventional pharmaceutically acceptable carriers and additives, and topical treatment of skin tumors with suitable topical compositions.

The invention further relates to a method of photodynamic therapy of cancer which comprises administering to a patient afflicted with a solid tumor cancer a pharmaceutical composition comprising a Chl or Bchl derivative according to the invention, and then irradiating the tumor site with strong light sources at 670–780 nm.

Several applications are thus foreseen for the Chl and Bchl derivatives of the invention, such as for photodestruction of benign or malignant cells or tissue by site-directed photodynamic therapy (SDP). The conjugate carries the Chl or the Bchl molecule to the cells that cluster in tumor tissues upon transformation, but are well separated from each other in normal tissues (e.g. melanocytes in melanoma). As a result, the photodynamic effect of the photosensitizer in the tumor can be higher by orders of magnitude than its effect in the normal tissue. Consequently the threshold of illumination that is destructive for the tumor is expected to be reduced to a level that is non-destructive for the normal tissue. Under these circumstances, the phototoxic effect will be limited to the tumor site even under non-specific irradiation. This application is of a particular importance for tumors that are inaccessible to conventional surgery.

Photodynamic therapy using biphotonic processes (Leupold and Freyer, 1992) is another way to extend the range of sensitization to the near-IR. The high inter-system crossing rate of the Chl and Bchl derivatives and their long wavelength for maximum absorption make them very good candidates for this mode of PDT.

The conjugates of the invention are also useful for photodestruction of normal or malignant animal cells as well as of microorganisms in culture with or without SDP, enabling selective photodestruction of certain types of cells in culture or infective agents; for targeting of the porphyrin moiety to selected cells by attachment of, for example, a Chl- or Bchl-serine conjugate to specific polypeptides, such as hormones or other receptor ligands, to cell- or tissue-specific antibodies or to other ligands, e.g., lectins; for fluorescent labeling/tagging of molecules for analytical purposes in laboratory, diagnostic and industrial applications; and for fluorescent labeling of animal cells or microorganisms or particles for laboratory, diagnostic or industrial applications. They can replace several of the currently used fluorescence tags, such as fluorescein isothiocyanate (FITC) or phycoerythrine, due to their superior extinction coefficients and higher fluorescence yield.

For diagnostic purposes, the Chl and Bchl derivatives of the invention, can be radioactively-labeled by standard procedures, e.g., with $^{67}$Ga, $^{111}$In, $^{201}$Tl, $^{99m}$Tc, and the radioactive diagnostic agent is administered to the patient, preferably by i.v. injection. After some hours, the locus of the cancer may be imaged by standard procedures.

The expected benefits of PDT using site-directed sensitizers as those of the invention consist in dramatic decreases in side effects and in the applied doses of sensitizers. Some particular advantages of using the proposed Chl and BChl derivatives of the invention for PDT are as follows:

1. A previously inaccessible functional group of the Chls and BChls, i.e. the C-$13^3$ ester group has been rendered accessible, alone or in combination with the C-$17^3$ ester group, for transesterification, thioester formation or amidation. The obtained pigments retain their favorable absorption and other optical and excited state properties, while allowing for the better adjustment of hydrophilic/hydrophobic balance and/or targeting.

2. These compounds have maximum optical absorption at wavelengths where the optical absorption/attenuation by human/animal tissues greatly decreases (660–830 nm in the monomeric form and up to 1000 nm in dimers or higher aggregates). Together with a decrease in light scattering, this should allow greater depth of penetration or the use of less intense and expensive light sources.

3. Their extinction coefficients in the visible and near-IR are approximately ten times larger than those of the porphyrins currently employed for PDT.

4. The procedure is mild enough to retain the native Mg, atom. However, substitution of the central Mg atom by other metals is possible and can enhance the yield of singlet oxygen production due to a higher triple state yield of the photosensitizer and can stabilize the compounds significantly.

5. The Chl and Bchl sensitizers of the invention should display increased specificity for recognition of the target cells and, therefore, lower doses should be sufficient for cell necrosis. In addition, they display superior photochemical properties over many presently used fluorophores and may, therefore, be practical in other applications.

6. There are some reports indicating a high clearance rate of certain Chl derivatives from the body (Spikes and Bommer, 1991).

7. Usually, the irradiation in PDT is carried out with laser sources such as Ar-pumped dye laser tuned to emit at 630 nm or gold-vapor laser (pulsed) that emits at 628 nm. The high cost of this equipment limits the application of PDT to larger medical centers. The use of red or near-IR absorbing photosensitizers according to the invention opens the way to more conventional and low cost means, such as Xenon flash lamps, halogen lamps, diode lasers or direct solar radiation.

8. Radioactively or actively labeled Chl and BChl derivatives can be used simultaneously for both diagnostic and therapeutic purposes.

The invention will now be illustrated by the following non-limiting examples.

EXAMPLES

General Procedures (a) Diesters preferentially modified at the C-$13^2$ carboxylic acid group of (bacterio)chlorophyll derivatives may be prepared by the following method:

The (bacterio)chlorophyll derivative (3 mg, 4 μmol) is dissolved in 15 ml dry and peroxide-free tetrahydrofuran (THF) (or in dimethylformamide (DMF) in the case of THF-insoluble alcohols). A 500-fold surplus of alcohol and 1 μl (4 μM) of tetraethyl-ortho-titanate are added to the reaction solution. The mixture is kept at 75° C. for 2, 8 or 14 days, in case of 1-propanol, para-tert-butyl-benzyl alcohol or N-tBoc-serine, respectively. Reaction mixtures are usually worked-up by: (i) addition of diethyl ether and water until phase separation occurs; (ii) three-fold extraction of aqueous phase with ether; (iv) drying of the combined organic phases with NaCl; (v) evaporation of the solvent in vacuum, and (vi) removal of excess alcohol in high vacuum ($<10^{-3}$ Pa).

(b) Transesterification at both C-$13^3$ and C-$17^3$ may be performed simultaneously according to the above procedure, with the difference that the alcohol is used as a solvent[2]. The reaction time for the para-tert-butyl-benzyl alcohol and for n-propanol are 48 and 12 h, respectively.

[2] Not applicable for NtBoc-ser, which is a solid.

Several esters were prepared by the above methods (a) and (b) using, for example, methanol, ethanol propanol, tert-butyl-benzyl alcohol, tert-butyloxycarbonyl-serine and serine. Examples of such esters of formulas I, II and III according to Scheme B can be found in Table 1 herein. These derivatives can be used themselves in the application of the invention or they can serve as bridge/spacer to link other suitable molecules to the Chl and BChl macrocycles.

(c) Treatment of the transesterified esters of formulas I, II and III obtained as above with pyridine at high temperatures provide the pyro-derivatives of formulas IV and V in Scheme B, examples of which can be found in Table 2 hereinafter.

Example 1

Preparation of $13^3$-tert-butyl-benzyl-Pd-bacteriopheophorbide-a-$17^3$-methyl ester (tbb-Pd-BPheid-me) ($R_1$-tbb; $R_2$—$CH_3$; M-Pd)

Following the general procedure (a) above, 3 mg of Pd-BPhe-me were reacted with 250 μl of para-tert-butylbenzyl alcohol (tbb). After 10 days, the main product tbb-Pd-BPheid-me was isolated in 65% yield after chromatography on silica with acetone/toluene 5:95 (v/v). The diester $13^3$-tert-butylbenzyl-Pd-bacteriopheophorbide a-$17^3$-tert-butyl-benzyl ester (tbb-Pd-BPheid-tbb) was isolated as a by-product.

Analytical data for tbb-Pd-BPheid-me:

$t_r$=16.3 min on HPLC-system HIII: $r_f$=0.27 on silica with acetone/toluene=5:95 (v/v). UV/Vis: $\lambda_{max}$ [nm] ($A_{rel}$) assignment=332 (0.67) $B_y$, 385 (0.53) $B_x$, 530 (0.19) $Q_x$, 755 (1) $Q_y$. $^1$H-NMR: δ [ppm] (multiplicity, assignment)=9.57 (s, 5-H), 8.67 (s, 10-H), 8.63 (s, 20-H), 7.48 and 7.28 (2 d, $^3J_{A'B'}$=$^3J_{AB}$=4 Hz, o- and m-H of tbbat C-$13^3$), 6.52 (s, $13^2$-H), 5.53 (s, $13^3$-$CH_2$), 4.37, 4.14, 4.11, 3.97 (4 m, 7-H, 8-H, 17-H and 18-H), 3.50 ($17^3$-$COOCH_3$), 3.06 ($3^1$-$COCH_3$), 3.41 (s, 12-$CH_3$), 3.39 (s, 2-$CH_3$), 2.60–2.01 (m, $17^{1,2}$-$CH_2$), 1.63 (m, 7-$CH_3$), 0.98 (t, $^3J_{AB}$=7 Hz, $8^1$-$CH_3$), 1.18 (s, tbb-$CH_3$ at $13^3$) MS (FAB): $M^+$=860.0 (calculated 860.4 for $^{12}C_{46}{}^1H_{50}{}^{14}N_4{}^{16}O_6{}^{106}Pd$), 669.39 (35%, $M^+$–COO-tbb); 713.3 (18%, $M^+$–tbb); 877 (30%, addition of O and H); 819 (17%, addition of O and H plus loss of $HC(CH_3)_3$).

Example 2

Preparation of $13^3$-tert-butyl-benzyl-Pd-bacteriopheophytin-a-$17^3$-geranylgeranyl ester (tbb-Pd-BPhe-gg)

3 mg Pd-BPhe-gg was transesterified with 250 μl of para-tert-butylbenzyl alcohol (tbb). After 14 days at 75° C. tbb-Pd-BPhe-gg was isolated in 63% after chromatography on silica with acetone/toluene=5:95 (v/v).

Analytical data for tbb-Pd-BPhe-gg: $t_r$=16.3 min on HPLC (silica, gradient 3–10% A in B, with A=toluene, B: toluene/methanol/n-propanol=100:4:0.5 (v/v/v), flow rate=1 ml/min); $r_f$=0.63 on silica with acetone/toluene=5:95 (v/v).

UV/Vis: $\lambda_{max}$ [nm] ($A_{rel}$, assignment)=332 (0.51 $B_y$), 384 (0.42, $B_x$), 528 (0.45, $Q_x$), 756 (1, $Q_y$). $^1$H-NMR: δ [ppm] (multiplicity, assignment)=9.58 (s, 5-H), 8.67 (s, 10-H), 7.49 and 7.24 (2m, o- and m-H of $13^3$-tbb), 6.53 (s, $13^2$-H), 5,54 (s, $13^3$-$CH_2$), 4.37, 4.14, 4.11, 3.97 (4m, 7-H, 8-H, 17-H and 18-H), 3.08 (s, 3-$COCH_3$), 3.41 (s, 12-$CH_3$), 3.39 (s, 2-$CH_3$), 3.50 (s, $17^3$-$COOCH_3$), 4.61 (m, gg-$OCH_2$), 5.15 (m, gg-$OCH_2$—$CH$), 1.63 (s, gg-$CH_3$), 2.59–1.98 (4m, 17-$CH_2$), 1.18 (s, $13^3$-tbb-$C(CH_3)_3$), 1.69 (d, $^3J_{AB}$=7 Hz, 18-$CH_3$), 0.98 (t, $^3J_{AB}$=7 Hz, $8^1$-$CH_3$—) MS (FAB) $M^+$=1118,6 (calculated=1118.6 for $^{12}C_{65}{}^1H_{80}{}^{14}N_4{}^{16}O_6{}^{106}Pd$), 927 (<5%, $M^+$–COO-tbb).

Example 3

Preparation of $13^3$-propyl-Pd-bacteriopheophytin-a-$17^3$-geranylgeranyl ester (pr-Pd-BPhe-gg)

6 mg Pd-BPhe-gg were transesterified with 1 ml of 1-propanol (prOH) in 20 ml THF. After 14 days at 75° C., pr-Pd-BPhe-gg was isolated in 60% yield after chromatography on silica with acetone/toluene=5:95 (v/v).

Analytical data for tbb-Pd-BPhe-gg: $r_f$=0.44 on the system silica with acetone/toluene=5:95 (v/v).

UV/Vis: $\lambda_{max}$ [nm] ($A_{rel}$, assignment)=332 (0,50, $B_y$), 384 (0,44. $B_x$), 528 (0,47, $Q_x$), 756 (1, $Q_y$). $^1$H-NMR: δ [ppm] (multiplicity, assignment)=9.59 (s, 5-H), 8.66 (s, 10-H), 6.53 (s, $13^2$-H), 4.38, 3.90, 3.89, 3.97 (4 m 7-H, 8-H, 17-H and 18-H), 3.08 ($3^1$-$COCH_3$), 3.42 (s, 12-$H_3$), 3.39, (s, 2-$CH_3$), 4.71 (m, gg-$OCH_2$ at $17^3$), 5.46 (m, gg-$OCH_2$—$CH$ at $17^3$), 1.62 (s, gg-$CH_3$ at $17^3$), 2.59–1.98 (4 m, $17^{1,2}$-$CH_2$), 1.74–1.56 (m, propyl-$OCH_2CH_2$ at $13^3$), 0.98 or 0.62 (m, propyl-$CH_3$ at $13^3$). MS (FAB) $M^+$=1014.4 (calculated 1014.4 for $C_{57}H_{72}N_4O_6{}^{106}Pd$), 927 (<3%) ($M^+$–COO-pr).

Example 4

Preparation of $13^3$-tert.-butyloxycarbonyl-seryl-Pd-BPheid-a-$17^3$-methyl ester (N-tBoc-ser-Pd-BPheid-me)

50 mg of tert.-butyloxycarbonylserine (N-tBoc-ser) were added to a pigment-solution of Pd-BPheid-me in DMF. After 14 days at 75° C. N-tBoc-ser-Pd-BPheid-me was isolated in 7% yield by partition between water and ethyl-acetate and chromatography on silica with acetone/toluene=5:95 (v/v).

Analytical data for N-tBoc-ser-Pd-BPheid-me: $r_f$=0.03 on system silica with acetone/toluene=10:90 (v/v).

UV/Vis: (CHCl$_3$) $\lambda_{max}$ [nm] (A$_{rel}$, assignment)=332 (0,45, B$_y$), 387 (0,34, B$_x$), 537 (0,16), 764 (1, Q$_y$). MS (ESI) M$^+$=901,2 (calculated=901.4 for $^{12}$C$_{43}$$^1$H$_{49}$$^{14}$N$_5$$^{16}$O$_{10}$$^{106}$Pd), 845,4 (40%, addition of H and loss of C(CH$_3$)$_3$; 801,5 (10%, addition of H plus loss of NtBoc); 669 (11%, loss of NtBoc-ser).

Example 5

Preparation of 13$^3$-O-seryl-Pd-bacteriopheophorbide-a-17$^3$-methyl ester (O-ser-Pd-BPheid-me)

The protection-group of the compound of Example 4 was cleaved off by addition of 2 ml trifluoroacetic acid to the dry N-tBoc-ser-Pd-BPheid-me. The trifluoroacetic acid was removed within 15 min by an argon-stream and the residue extracted carefully three times with ethyl-acetate and water, to yield ser-Pd-BPheid-me (<5%) from Pd-BPheid-me. The pigment was purified on silica with acetone/toluene=40:60 (v/v) (further purification can be left out of consideration for the reaction to ser-Pd-BPheid-me).

Analytical data for ser-Pd-BPheid-me: $r_f$=0.65 on C$_{18}$ reverse-phase silica with methanol/toluene=5:95 (v/v).

UV/Vis: (CHCl$_3$) $\lambda_{max}$ [nm] (A$_{rel}$, assignment)=334 (0.36, B$_y$), 387 (0.29, B$_x$), 534 (0.09, Q$_x$), 765 (1, Q$_y$). MS (ESI) M$^+$=801.2 (calculated 801.3 for $^{12}$C$_{38}$$^1$H$_{41}$$^{14}$N$_5$$^{16}$O$_8$$^{106}$Pd); 698.3 (10%, addition of H and loss of serine).

Example 6

Preparation of 13$^3$-methyl-Pd-bacteriopheophorbide-a-17$^3$-n-propylester (me-Pd-BPheid-pr)

Using 7% n-propanol in THF, the by-product pr-Pd-BPheid-me was isolated during the synthesis of pr-Pd-BPheid-pr in 5% yield after chromatography on silica with acetone/toluene=5:95 (v/v).

Analytical data of me-Pd-BPheid-pr: $r_f$=0.42 on silica with acetone/toluene=10:90 (v/v).

UV/Vis: (DE) $\lambda_{max}$ [nm] (A$_{rel}$, assignment)=332 (0.50, B$_y$), 385 (0.38, B$_x$), 528 (0.15, Q$_x$), 755 (1, Q$_y$). $^1$H-NMR: δ [ppm]=9.57 (s, 5-H), 8.95 (s 10-H), 6.50 (s, 13$^2$-H), 4.32, 4.24, 3.88 (3 m, 7-H, 8-H, 17-H and 18-H), 3.87 (m, propyl-OCH$_2$ at 13$^3$), 3.07 (s, 3$^1$-COCH$_3$), 3.43 (s, 12-H$_3$), 3.38, (s, 2-CH$_3$), 2.62–2.09 (m, 17$^{1,2}$-CH$_2$), 1.72–1.56 (m, propyl-OCH$_2$CH$_2$, at 17$^3$-CH$_2$), 1.68 (m, 7-CH$_3$), 0.98 or 0.63 (m, propyl-CH$_3$ at 17$^3$) MS (ESI): M$^+$=756.6 (calculated 756.3 for $^{12}$C$_{38}$$^1$H$_{42}$$^{14}$N$_4$$^{16}$O$_6$$^{106}$Pd); 697.5 (27% M$^+$−COOCH$_3$).

Example 7

Preparation of 13$^3$-n-propyl-bacteriochlorophyllide-17$^3$-n-propylester (pr-BChlide-pr) (Central Metal Mg Instead of Pd)

Following the general procedure (b) above and starting from BChl with a 100-fold surplus of n-propanol, the product pr-BChlide-pr was obtained after 3 days in a yield of 40% after chromatography on C$_{18}$ reverse phase silica with a gradient 25–10% (phase A: HEPES/KOH (20 mMn pH 7.5), phase B: acetone).

Analytical data of pr-BChlide-pr: $r_f$=0.73 on C$_{18}$ reverse phase silica with HEPES/KOH (20 mM, pH 7.5)/acetone=15:85 (v/v).

UV/Vis: (DE) $\lambda_{max}$ [nm] (A$_{rel}$, assignment)=357 (0.78, B$_y$), 392 (0.52, B$_x$), 574 (0.23, Q$_x$), 771 (1, Q$_y$). $^1$H-NMR: δ [ppm] (multiplicity, assignment)=9.51 (s 5-H), 8.65 (s 10-H), 8.54 (s, 20-H), 6.57 (s 13$^2$-H), 4.35 (m, 7-H, 8-H, 17-H and 18-H), 3.99 (propyl-OCH$_2$ at C-17$^3$ and C-13$^3$), 3.11 (3$^1$-COCH$_3$), 3.57 (s, 12-CH$_3$), 3.46, (s, 2-CH$_3$), 2.62–2.09 (m, 17$^{1,2}$-CH$_2$), 1.63 (m, 7-CH$_3$), 0.81 (t, $^3$J$_{AB}$=7 Hz 8$^1$-CH$_3$) MS (ESI): M$^+$=702.4 (calculated 702.4 for $^{12}$C$_{40}$$^1$H$_{46}$$^{14}$N$_4$$^{16}$O$_6$$^{24}$Mg); 616.4 (addition of H and loss of COOC$_3$H$_7$).

Example 8

Preparation of 13$^3$-tert.-butyl-benzyl-Pd-bacteriopheophorbide-a-17$^3$-tert-butyl-benzyl ester (tbb-Pd-BPheid-tbb)

The reaction of the Pd-BPheid-me in para-tert-butyl-benzyl alcohol for 48 h yielded tbb-Pd-BPheid-tbb (50%) after chromatography on silica with acetone/toluene=5:95 (v/v).

Analytical data for tbb-Pd-BPheid-tbb: $t_r$=10,8 min on HPLC (silica, gradient 2–10% A in B, with A=toluene, B: toluene/methanol/n-propanol=100:4:0.5 (v/v/v):, $r_f$=0,50 on silica with acetone/toluene=5:95 (v/v), flow rate=1 ml/min).

UV/Vis: (DE) $\lambda_{max}$ [nm] (A$_{rel}$, assignment)=332 (0.49, B$_y$), 385 (0.36, B$_x$), 528 (0.15, Q$_x$), 755 (1, Q$_y$). $^1$H-NMR: δ [ppm] (multiplicity, assignment)=9.58 (s, 5-H), 8.75 (s, 10-H), 8.63 (s, 20-H), 7.50 and 7.26 (2 m, o- and m-benzyl-H at C-13$^3$), 6.53 (s 13$^2$-H), 5.53 (s, CH$_2$-group 13$^3$), 5,21, 5,16, 5,13, 5,03 (4 á s, 17$^3$-CH$_2$), 4.47, 4.22, 4.15, 3.97 (4 m, 7-H, 8-H, 17-H and 18-H), 3,06 (s, 3$^1$-COCH$_3$), 3,41 (s, 12-H$_3$), 3,38, (s, 2-CH$_3$), 2,36 (m, 17$^{1,2}$-CH$_2$), 1.63 (m, 7-CH$_3$), 0,95 (t, $^3$J$_{AB}$=7 Hz, 8$^1$-CH$_3$), 1.65 (d, $^3$J$_{AB}$=7 Hz, 18-CH$_3$), 1.2 and 1.8 tbb-C(CH$_3$)$_3$) MS (ESI): M$^+$=992.3 (calculated 992.5 for $^{12}$C$_{56}$$^1$H$_{62}$$^{14}$N$_4$$^{16}$O$_6$$^{106}$Pd); 1015 (20%, M$^+$+Na), 801.4 (24%, M$^+$−COO-tbb).

Example 9

Preparation of 13$^3$-n-propyl-Pd-bacteriopheophorbide-a-17$^3$-n-propyl ester (pr-Pd-BPheid-pr)

The transesterification was started with Pd-BPheid-gg in propanol following the general procedure. After 12 h, the product pr-Pd-BPheid-pr was obtained in 71% yield after chromatography on silica with acetone/toluene=5:95 (v/v).

Analytical data for pr-Pd-BPhe-pr: $r_f$=0.54 on silica with acetone/toluene=10:90 (v/v).

UV/Vis: (DE) (A$_{rel}$, assignment)=332 (0.48, B$_y$), 385 (0.41, B$_x$), 527 (0.15, Q$_x$), 755 (1, Q$_y$). $^1$H-NMR: δ [ppm] =9.58 (s, 5-H), 8.75 (s, 10-H), 8.65 (s, 20-H), 6.50 (s, 13$^2$-H), 4.38; 3.97, 3.89, 3.80 (4 m, 7-H, 8-H, 17-H and 18-H), 3.07 (s, 3$^1$-COCH$_3$), 3.89–3,83 (m, 2 H, propyl-OCH$_2$ at 17$^3$), 3.42 (s, 12-CH$_3$), 3.39, (s, 2-CH$_3$), 2.80–2.00 (m, 17$^{1,2}$-CH$_2$), 1.74–1.56 (m, H propyl-OCH$_2$CH$_2$ at 17$^3$ and 13$^3$), 1.63 (m, 7-CH$_3$), 1.70 (s, 18-CH$_3$), 0.98 and 0.62 (t, $^3$J$_{AB}$=7 Hz, propyl-CH$_3$ at 17$^3$ and 13$^3$). MS (ESI): M$^+$=784.7 (calculated 784.4 for $^{12}$C$_{40}$$^1$H$_{46}$$^{14}$N$_4$$^{16}$O$_6$$^{106}$Pd); 697.5 (17%, M$^+$−COOC$_3$H$_7$).

Example 10

Pyro-bacteriochlorophyllide-a-17$^3$-n-proplester (pyro-BChlide-pr) (Formula V in Scheme B, Central Metal Mg Instead of Pd)

After 6 days pyro-BChlide-gg yielded pyro-BChlide-pr (30%) after chromatography on silica with acetone/toluene=5:95 (v/v).

Analytical data of pyro-BChlide-pr: $r_f$=0.76 on $C_{18}$ reverse phase silica with HEPES/KOH (20 mM, pH 7.5)/acetone=15:85 (v/v).

UV/Vis: (DE) $\lambda_{max}$ [nm] ($A_{rel}$, assignment)=357 (0.75, $B_y$) 391 (0.52. $B_x$) 575 (0.21, $Q_x$) 771 (1, $Q_y$) $^1$H-NMR: δ [ppm] (multiplicity, assignment)=9.48 (s, 5-H), 8.65 (s, 10-H), 4.50–4.00 (4 m, 7-H, 8-H, 17-H and 18-H), 3.11 ($3^1$-COCH$_3$), 3.57 (s, 12-CH$_3$), 3.46, (s, 2CH$_3$), 2.73–2.09 (m, 17-CH$_2$-groups), 1.63 (m, 7-CH$_3$), 0.81 (s, $8^1$-CH$_3$), 1.70 (s, 18-CH$_3$), 1.75 (m, H propyl-OCH$_2$ at $17^3$) MS (ESI): M$^+$=616.5 (calculated 616.3 for $^{12}C_{36}{}^1H_{40}{}^{14}N_4{}^{16}O_4{}^{24}Mg$)

Example 11

Pyro-Pd-bacteriopheophorbide a-$17^3$-tert-butyl-benzyl ester (pyro-Pd-BPheid-tbb) (Formula V in Scheme B)

(a) Pyro-Pd-BPheid-me was reacted for 48 h with para-tert-butylbenzyl alcohol to yield pyro-Pd-BPheid-tbb. (b) Starting from pyro-Pd-BPhe-gg, same product was obtained under otherwise identical conditions in 70% yield after chromatography on silica with acetone/toluene=5:95 (v/v).

Analytical data of pyro-Pd-BPheid-tbb: $r_f$=0.25 on silica with acetone/toluene=5:95 (v/v).

UV/Vis: (DE) $\lambda_{max}$ [nm] ($A_{rel}$, assignment)=332 (0.50, $B_y$), 384 (0.37, $B_x$), 530 (0.15, $Q_x$), 755 (1, $Q_y$) $^1$H-NMR: δ [ppm] (multiplicity, assignment) 9.63 (s, 5-H), 8.73 (s, 10-H), 7.31 s, o- and m-benzyl-H at C-$13^3$), 5.09 and 5.18 (dd $^2J_{AA'}$=12 Hz, $13^2$-H), 5.12 and 5.17 (dd, $^3J_{AA'}$=6 Hz, CH$_2$ C-$17^3$), 4.8, 4.36, 4.25, 4.02 (4 m, 7-H, 8-H, 17-H and 18-H), 3.07 (s, $3^1$-COCH$_3$), 3.48 (s, 12-CH$_3$), 3.40 (s, 2-CH$_3$), 2.78–2.33 (m, $17^{1,2}$-CH$_2$) 1,58 (m, 7-CH$_3$), 0.99 (t, $^3J_{AB}$=8 Hz, 8-CH$_3$), 1.68 (d, $^3J_{AB}$=7 Hz 18-CH$_3$), 1.17 (ttbb-C(CH$_3$)$_3$) MS (FAB): M$^+$=802.1 (calculated 802.4 for $^{12}C_{44}{}^1H_{48}{}^{14}N_4{}^{16}O_4{}^{106}Pd$).

Example 12

Preparation of Pd-bacteriopheophorbide a-$17^3$-N-glucosamide (Pd-BPheid-Nglc) (Formula VI in Scheme C)

Another reaction mechanism results in derivatives where the ester group at C-$17^3$ is replaced by the more stable amide bond (see Scheme C).

In a carefully dried apparatus, 60 mg (88 μmol) of the free acid Pd-BPheid were dissolved in 20 ml dry DMF. After the flask was cooled to 0° C., 70 mg (324 μmol) of glucosamine hydrochloride were added. The pH-value, was adjusted to 8–9 with 31.2 μl (317 μmol) of diisopropyl-ethyl-amin. For measuring the pH, a drop of the reaction mixture and a drop of water were mixed on a strip of pH-indicator paper. 30 mg (91 μmol) of TBTU (2-(1H-benzotriazol-1-yl)-1,1,3,3-tetramethyluronium tetrafluoroborate) were added, and the flask kept for 16 h at room temperature. The flask was allowed to warm up to room temperature overnight. Ther reaction mixture was partitioned between chloroform and water. Any resulting precipitate was removed by filtration. The chloroform-phase was removed and the pigment was dried with toluol in a rotavapour. The product is obtained in 20% yield after chromatography on the system SII.

Analytical data of Pd-BPheid-Nglc: $r_f$=0.75 on $C_{18}$ reverse-phase silica with methanol.

UV/Vis: (CHCl$_3$) $\lambda_{max}$ [nm] ($A_{rel}$, assignment)=334 (0.32, $B_y$), 388 (0.27, $B_x$), 537 (0.11, $Q_x$), 763 (1, $Q_y$). $^1$H-NMR: δ [ppm] (multiplicity, assignment)=9.58 (s, 5-H), 8.95 (s, 10-H), 8.46 (s, 20-H), 6.37 (s, $13^2$-H), 4.51, 4.41, 3.83, (3 m, 7-H, 8-H, 17-H and 18-H), 3.07 (s, $3^1$-COCH$_3$), 3.43 (s, 12-CH$_3$), 3.37, (s, 2-CH$_3$), 1.68 (m, 7-CH$_3$), 3.85 (s, $13^2$-COOCH$_3$), 2.8–2.0 (m, $17^{1,2}$-CH$_2$) MS (ESI): M$^+$=875.1 m/z (calculated 875.3 for $^{12}C_{41}{}^1H_{47}{}^{14}N_5{}^{16}O_{10}{}^{106}Pd$); 898.1 (M$^+$+Na$^+$).

Example 13

Phototoxicity of M-BChl Derivatives to Melanoma Cells in Cultures

Liposome Preparation

L-α-Dipalmitoylphosphatidylcholine (DPPC) liposomes as carrier system for pigments insoluble in water were prepared according to Toledano, 1998 and to Cuomo et al. 1990. 1.4×10$^{-8}$ moles (≅130 μg) of the photosensitizer and 5 mg DPPC were dissolved in 400 μl chloroform. Onto this were layered 250 μl H$_2$O and 250 μl phosphate buffer (pH=7,2; 1,5 mM KH$_2$PO$_4$; 7,6 mM Na$_2$HPO$_4$; 0,15 M NaCl). The chloroform was removed within 5 min with a rapid stream of argon, while the mixture was sonicated and maintained at 45° C. Sonication was continued for another 20 min and the liposomes loaded with pigment were recovered in the supernatant after centrifugation (16 000×g, 10 min). The liposome concentration was determined photometrically at 750 nm (according to Grossweiner and Grossweiner, 1982).

Photodynamic Activity in Monolayer Cell Culture

M$_2$R melanoma cells (mice) were cultivated as monolayers in 96-well microtiter-plates in DMEM (Dulbecco's modified Eagle's medium)/F$_{12}$ 1/1 (v/v) at 37° C. in a moist atmosphere containing 8% CO$_2$. The medium (pH 7.4) was supplemented with HEPES buffer (25 mM), fetal-bovine-serum (FBS) (10%), glutamine (2 mM), penicillin (0.06 mg/ml) and streptomycin (0.1 mg/ml). Within 24 hrs, the cell density increased from 1×10$^4$ to 2×10$^4$ cell/100 μl. Increasing amounts of the liposome preparation containing the BChl-derivative were added to the cells. (Pd-BPheid-ser or Pd-BPheid-Nglc were added as ethanolic solution (10$^{-4}$ M) such that the maximum concentration of ethanol was <1%). The cells were first kept in the dark for 4 hrs, washed with 100 μl of the medium, treated with 100 μl of fresh medium, and then irradiated from below through the bottom of the plates with a russian BS LS3-PDT lamp, fitted with a filter (600–1300 nm). A light-dose of 10 mW x s x cm$^{-2}$ was provided during an irradiation time of 10 mm. After an additional 24 h in the dark at 37° C., cell viability was determined by microscopic inspection (cell size and shape) and via [$^3$H]-thymidine incorporation into the DNA (Chen et al. 1988). For the latter, cells were incubated at the end of the experiment for 2 h at 37° C. with 1 μCi/ml [$^3$H] thymidine (in water). They were then washed twice with phosphate buffer, incubated with 7.5% cold trichloroacetic acid for 30 min at 4° C., washed again with 95% ethanol, and finally treated with 200 μl 1N NaOH for 10 min at 37° C. 100 μl of the final suspension in NaOH were removed, neutralized with 100 μl 1N HCl, mixed with 4 ml scintillation liquid (20:8 (v/v) xylene:scintillator Lumax mix) and 5 ml imidazole-buffer (0.1 M).

Figure 1A:
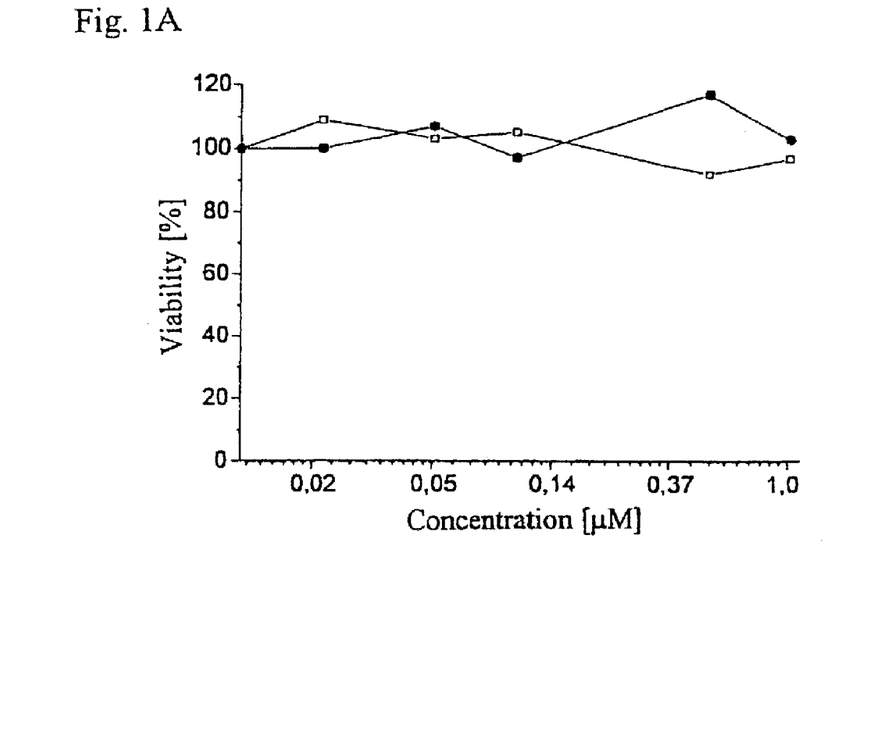
FIGS. 1A–1D show toxicity in the dark (black squares) and photocytotoxicity (white squares) to $M_2R$ melanoma cells after incubation with tbb-Pd-BPheid-tbb (1A), tbb-Pd-BPheid-me (1B), Pd-BPheid-et (1C), control (1D). Sensitizers were added in liposomes. Cell viability was determined by [$^3$H]-thymidine incorporation into DNA.
Figure 1B:
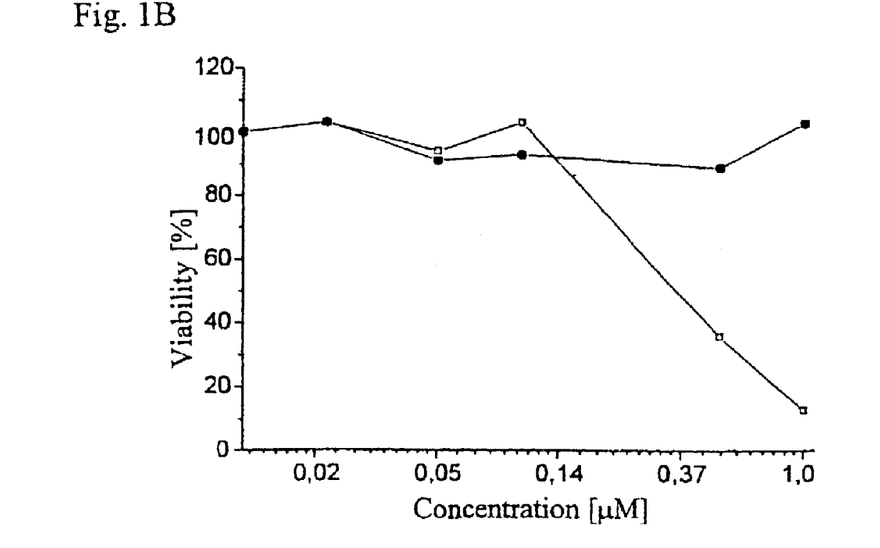
Figure 1C:
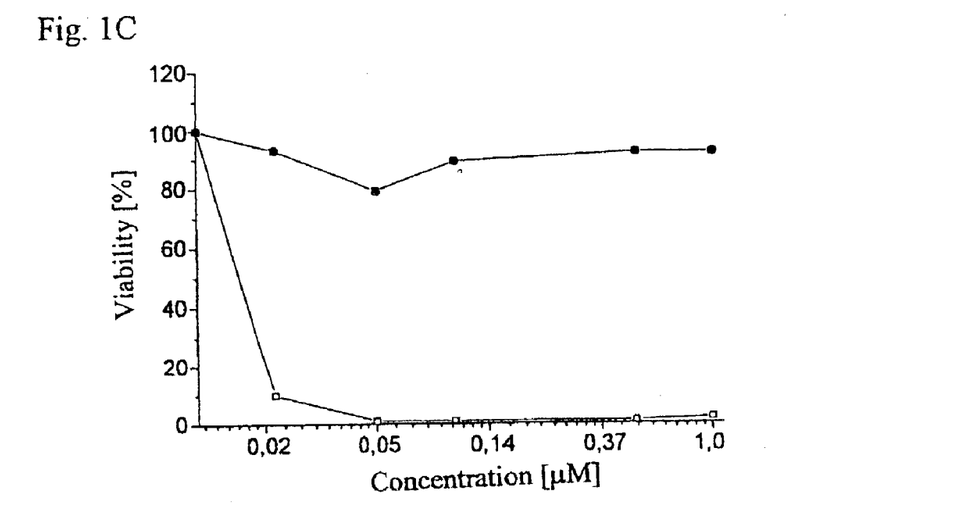
Figure 1D:
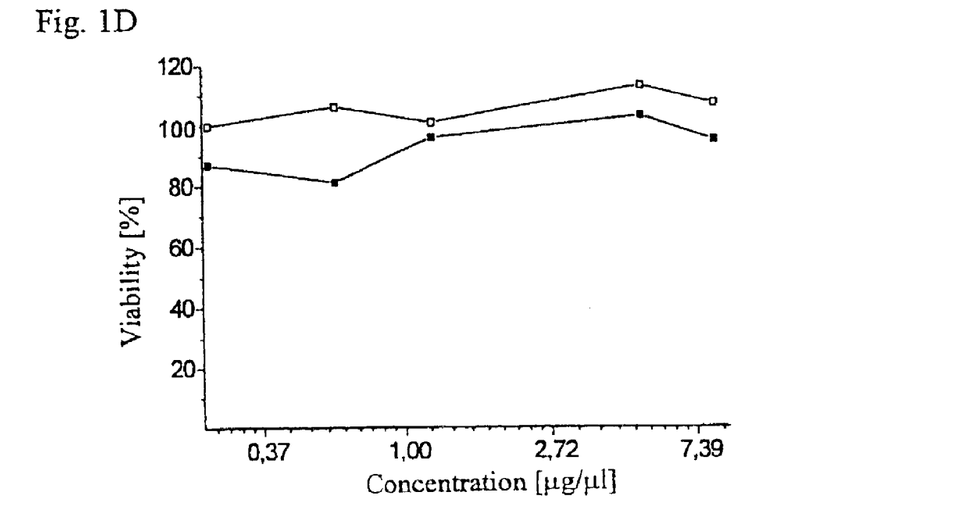
Figure 2:
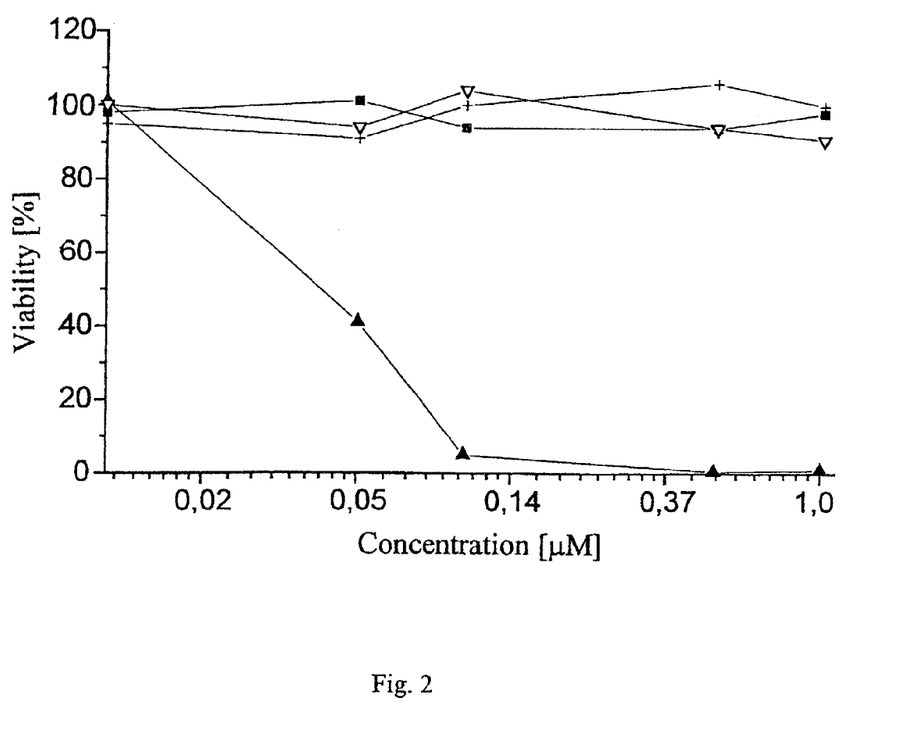
FIG. 2 shows toxicity in the dark (-+-) and photocytotoxicity of Pd-BPheid-Nglc (black squares) and of Pd-BPheid-ser light (black triangles), dark (white triangles) of mouse $M_2R$ melanoma cells. Cell viability was determined by [$H^3$]-thymidine incorporation.

The results are shown in FIGS. 1 and 2. Three of the sensitizers shown in FIGS. 1 and 2 were phototoxic to mouse M2R melanoma cells (Pd-Bpheid-et (LD$_{90}$=0.02

μM) and tbb-Pd-Bpheid-me (LD$_{90}$=1.1 μM)), Pd-BPheid-ser ((LD$_{90}$=0.1 μM). tbb-Pd-BPheid-tbb and Pd-BPheid-Nglc are ineffective under these conditions because they formed aggregates in the liposomes which are ineffective for PDT.

TABLE 1

[M]-BPhe transesterified selectively at C-13$^3$ or simultaneously at C-13$^3$ and C-17$^3$

| Compound: | formula (Scheme B) | R$_2$ | R$_1$ | R$_1$ | M |
|---|---|---|---|---|---|
| Me-BChl-gg | I | gg | me | — | Mg |
| Me-Pd-BPhe-me | I | me | me | — | Pd |
| Me-Pd-BPhe-gg | I | gg | me | — | Pd |
| Tbb-Pd-BPhe-tbb | III | tbb | — | tbb | Pd |
| Tbb-Pd-BPhe-me | II | me | — | tbb | Pd |
| Tbb-Pd-BPhe-gg | II | gg | — | tbb | Pd |
| NtBoc-ser-Pd-BPhe-me | II | me | — | ser | Pd |
| Pr-Pd-BPhe-pr | III | pr | — | pr | Pd |
| Me-Pd-BPhe-pr | II | pr | — | me | Pd |
| Pr-Pd-BPhe-gg | II | gg | — | pr | Pd |
| Pr-BChl-pr | III | pr | — | pr | Mg |

TABLE 2

Transesterification products of pyro-[M]-BPhe.

| Compound: | formula (Scheme B) | R$_1$ | R$_1$ | M |
|---|---|---|---|---|
| Pyro-BChl-gg | IV | gg | | Mg |
| Pyro-Pd-BPhe-gg | IV | gg | | Pd |
| Pyro-Pd-BPhe-tbb | V | — | tbb | Pd |
| Pyro-Pd-BPhe-pr | V | — | pr | Pd |
| Pyro-BChl-pr | V | — | pr | Mg |

Scheme A a) Structure of Chlorophyll a and the IUPAC numbering system b) Structure of Bacteriochlorophyll a Scheme B:
Reaction scheme for preparation of bacteriochlorophyll derivatives transesterified at C-13³ and/or C-17³.

Scheme C-
Coupling of glucosamine to C-17³ of Pd-Bpheid

VI - R₄ is the residue of glucosamine

REFERENCES

Beems, E. M., Dubbelman, T. M. A. R. Lugtenburg, J., van Best, J. A., Smeets, M. F. M. A., & Boegheim, J. P. J. (1987) Photochem. Photobiol. 46, 639–644.

L. Chen, S. Gross, V. Rosenbach-Belkin, A. Brandis, Y. Salomon and A. Scherz (1988) Microbial photoinactivation by serine and IgG conjugates of chlorophyll and bacteriochlorophyll. In: *Proceedings of the 7th Biennial Congress,. International Photodynamic Association*, (ed T. Patrice)

Cuomo, V.; Jori, G.; Rither, B. and Denney, M. E. R. M. A. J. (1990). Br. J. Cancer. 62: 966–970.

Dougherty, T. J. (1992) Bacteriochlorophyll a Derivatives Useful in Photodynamic Therapy., U.S. Pat. No. 5,171,741, USA. Int. Class A61K31/40, Appl. No. 341,591.

Fiedor, L., Gorman, A. A., Hamblett, I., Rosenbach Belkin, V., Salomon, Y., Scherz, A., & Tregub, I. (1993) Photochem Photobiol 58, 506–511.

Fiedor, L., Rosenbach-Belkin, V., M. Sai and A. Scherz (1996) Preparation of tetrapyrrole-amino acid covalent complexes. *Plant Physiol. Biochem.* 34, 393–398

S. Gross, A. Brandis, L. Chen, V. Rosenbach-Belkin, S. Roehrs, A. Scherz and Y. Salomon (1997) Protein A mediated Bacteriochlorophyll-IgG targeting to *Staphylococcus aureus*: A model for enhanced site-specific photocytotoxicity. *Photochem. Photobiol.* 66, 872–878

Grossweiner, L. I. P. A. S. and Grossweiner, J. B. (1982). Photobiol. 36: 159–167.

Hunt, J. E., & Michalski, T. J. (1991). Chlorophylls, H. Scheer. (ed.) Boca Raton: CRC Press.

Hynninen, P. H. (1991) in 'Chlorophylls' (Scheer, H., ed.), pp 145–210, CRC-Press, Boca Raton.

Imwinkelried, R, Schiess, M., & Seebach, D. (1987). Org. Synth. 65, 230–235.

S. Katz, Y. Vakrat, V. Brumfeld, L. Weiner, E. Gabelman, A. Brandis, A. Paul, M. Hild, R. Lendt, D. Leopold, J. R. Norris, Y. Salomon and A. Scherz (1998), Bacteriochlorophyll-serine generates only hydroxy radicals under near infra-red illumination. In: *Proceedings of the 7th Biennial Congress,. International Photodynamic Association*, (ed. T. Patrice)

D. K. Kelleher, O. Thews, J. Rzeznik, A. Scherz, Y. Salomon and P. Vaupel (1999) Water-filtered infrared-A radiation: a novel technique for localized hyperthermia in combination with bacteriochlorophyll-based photodynamic therapy, Int. J. of Hyperthermia (In press)

Kessel, D., Smith, K. M., Pandey, R. K., Shiau, F. Y., & Henderson, B. (1993) Photochem. Photobiol. 58, 200–203

Moser, J. G. (ed.) (1998) Photodynamic Tumor Therapie, $2^{nd}$ and $3^{rd}$ Generation Photosensitisers, Harwood Academic Publishers, Netherlands Neises, B. & Steglich, W. (1978). Angew. Chem. 90, 556.

Pandey, R. K., Shiau, F. Y., Sumlin, A. B., Dougherty, T. J., & Smith, K. M. (1994) Bioorg Med. Chem. Let. 4, 1263–1267.

Pennington, F. C., Strain, H. H., Svec, W. A., & Katz, J. J. (1963). J. Am. Chem. Soc. 86:1418–26.

Rehwinkel, H. & Steglich, W., (1982) Synth. Comm. 827.

V. Rosenbach-Belkin, L. Chen, L. Fiedor, Y. Salomon, and A. Scherz (1998) Chlorophyll and bacteriochlorophyll derivatives as photodynamic agents. In: *Photodynamic Tumor Therapy;* 2nd and 3rd Generation Photosensitizers (ed. J. G. Moser), Harwood Academic Publishers, Australia, 117–125

Scheer, H., (ed.) (1991), Chlorophylls, CRC-Press, Boca Raton.

A. Scherz, S. Katz, Y. Vakrat, V. Brumfeld, E. Gabellman, J. Zilberstein, D. Leopold, J. R. Norris, H. Scheer, and Y. Salomon (1998) Bacteriochlorophyll-serine based photochemotherapy; type III PDT? In: *"Photosynthesis: Mechanisms and Effects"* (*Ed. G. Garab*), Kluwer Acad. Publishers, Dordrecht, the Nederlands, V. V pp. 4207–4212

Schneider, C. H. & Eberle, A. N. (1992). Peptides. ESCOM Science Publishers B. V.

Schnurrenberger P., Züger M. F. & Seebach, D. (1982). Helv. Chim. Acta 65,1197–201.

Seebach, D., E. Hungerbühler, R. Naef, P. Schnurrenberger, B. Weidmann, & M. Züger. (1982). "Titanate-Mediated Transesterifications with Functionalized Substrates." Comm. Synth., 139–141 139–41.

Spikes, J. D. & Bommer, J. C. (1991) in 'Chlorophylls' (Scheer, H., ed.), pp 1181–1204, CRC-Press, Boca Raton.

Struck, A., Snigula, H., Rau, H.-K, Hörth, P., Scheer, H., Haehnel, W. in G. Carab (ed.): Photosynthesis: Mechanisms and Effects, Kluwer, 1999, pp. 4213–4216

Toledano, F.; Edrei, R. and Kimel, S. (1998) J. Photochem. Photobiol. B: Biol.: 42: 20–27.

Tregub, I., Rosenbach-Belkin, V., Fiedor, L., Azrad, A., Shai, E., Pavlotszky, F., Salomon, Y., & Scherz, A. (1993) Abstracts of the Fifth Congress of the European Society for Photobiology, 201.

J. Zilberstein, A. Bromberg, A. Franz, V. Rosenbach-Belkin, A. Kritzmann, R. Pfeferman, Y. Salomon and A. Scherz (1997) Light dependent oxygen consumption in bacteriochlorophyll-serine treated melanoma tumors: on line determination using a tissue inserted oxygen microsensor. Photochem. Photobiol. 65, 1012–1020

J. Zilberstein, V. Rosenbach-Belkin, A. Scherz, and Y. Salomon (1998) A novel tissue inserted optical oxygen microsensor: on-line determination of effective photodynamic therapy in solid melanotic melanoma tumors in: *Photodynamic Tumor Therapy; 2nd and 3rd Generation Photosensitizers.* (ed. J. G. Moser), Harwood Academic Publishers, Australia, 183–194

J. Zilberstein, V. Rosenbach-Belkin, M. Neeman, P. Bendel, F. Kohen, B. Gayer, A. Scherz and Y. Salomon (1998) Bacteriochlorophyll-based PDT of solid tumors relies on vascular destruction. In: *Proceedings of the 7th Biennial Congress,. International Photodynamic Association, (ed T. Patrice)*

J. Zilberstein, M. C. W. M Bloemers, M. Neeman, A. Scherz and Y. Salomon (1999) Therapy of solid melanoma tumors by vascular infarction and perfusion arrest in bacteriochlorophyll-serine base photochemotherapy, *Cancer Res.* Submitted.

What is claimed is:

1. A transesterification process for the preparation of a synthetic chlorophyll or bacteriochlorophyll derivative of the general formula I wherein M is a central metal atom selected from the group consisting of Mg, Pd, Co, Ni, Cu, Zn, Hg, Er, Ti, Eu, Sn and Mn or represents two H atoms;

$R_3$ and $R_5$ are each, independently, acetyl, vinyl, ethyl, 1-hydroxyethyl or an ether or ester of said 1-hydroxyethyl radical;

$R_4$ is methyl or formyl;

the dotted line at positions 7–8 represents an optional double bond; and $R_1$ and $R_2$ are different and are selected from the group consisting of:

(i) a $C_1$–$C_{25}$ hydrocarbyl radical that may be straight or branched, saturated or unsaturated, optionally substituted by one or more radicals selected from halogen, oxo (=O), OH, CHO, COOH, or $NH_2$, or interrupted by one or more heteroatoms selected from O, S and NH, or by carbocyclic or heterocyclic moieties;

(ii) a residue of an amino acid, an oligopeptide or a polypeptide containing a hydroxy group or of a derivative thereof selected from the group consisting of esters and N-protected derivatives, wherein said hydroxylated amino acid or derivative thereof is linked to the COO⁻residue of the Chl or BChl derivative through said hydroxy group;

(iii) a residue of a peptide as defined in (ii) linked to the COO⁻residue via a $C_1$–$C_{25}$ hydrocarbyl as defined in (i) wherein said $C_1$–$C_{25}$ saturated or unsaturated hydrocarbyl residue optionally substituted by one or more radicals selected from halogen, oxo (=O), OH, CHO, COOH, $NH_2$, or such a residue interrupted by one or more heteroatoms selected from O, S and NH, or by a phenyl ring is further substituted by an end functional group selected from OH, COOH, or $NH_2$;

(iv) a residue of a cell- or tissue-specific ligand selected from an oligo-peptide and a protein directly linked to the COO⁻residue or via a $C_1$–$C_{25}$ hydrocarbyl as defined in (i) wherein said $C_1$–$C_{25}$ saturated or unsaturated hydrocarbyl residue optionally substituted by one or more radicals selected from halogen, oxo (=O), OH, CHO, COOH, $NH_2$ or such a reside interrupted by one or more heteroatoms selected from O, S, NH, or by a phenyl ring, is further substituted by an end functional group selected from OH, COOH, or $NH_2$; and (v) a residue of a mono-, oligo- or polysaccharide or from a polyoxyethylene directly linked to the COO⁻residue or via a $C_1$–$C_{25}$ hydrocarbyl as defined in (i) wherein said $C_1$–$C_{25}$ saturated or unsaturated hydrocarbyl residue optionally substituted by one or more radicals selected from halogen, oxo (=O), OH, CHO, COOH of $NH_2$, or such a residue interrupted by one or more heteroatoms selected from O, S and NH, or by a phenyl ring, is further substituted by an end functional group selected from OH, COOH, or $NH_2$;

comprising the reaction under anaerobic conditions of a (bacterio) chlorophyll, metal-(bacterio)chlorophyll or (bacterio)pheophytin derivative carrying at position C-13² a $COOCH_3$ group and at position C-17² a $COOR_2$ group, with an alcohol $R_1OH$ with the proviso that $R_1$ is not methyl, in the presence of tetraethyl-ortho-titanate, wherein the reaction is performed in an aprotic solvent selected from peroxide-free tetrahydrofuran (THF) or dimethylformamide (DMF), thus obtaining the desired C-13²-$COOR_1$, C-17²-$COOR_2$ diester which is then separated from the reaction mixture.

2. A process according to claim 1, wherein M is a divalent metal selected from the group consisting of Mg, Pd, Co, Ni, Cu, Zn, Hg, Er, Ti, Eu, Sn and Mn.

3. A process for the preparation of a chlorophyll compound according to claim 1, wherein $R_3$ is vinyl, $R_4$ is methyl or formyl, $R_5$ is ethyl and the dotted line at positions 7–8 represents a double bond.

4. A process for the preparation of a bacteriochlorophyll compound according to claim 1, wherein $R_3$ is acetyl, $R_4$ is methyl, $R_5$ is ethyl and the positions 7–8 are hydrogenated.

5. The process according to claim 4, wherein M is Pd, $R_1$ is tert-butylbenzyl and $R_2$ is methyl.

6. The process according to claim 4, wherein M is Pd, $R_1$ is tert-butylbenzyl and $R_2$ is geranylgeranyl.

7. The process according to claim 4, wherein M is Pd, $R_1$ is propyl and $R_2$ is geranylgeranyl.

8. The process according to claim 4, wherein M is Pd, $R_1$ is N-tert-butyloxycarbonylseryl and $R_2$ is methyl.

9. The process according to claim 4, wherein M is Pd, $R_1$ is O-seryl and $R_2$ is methyl.

10. A transesterification process for the preparation of a synthetic chlorophyll or bacteriochlorophyll derivative of the general formula I wherein
- M is a central metal atom selected from the group consisting of Mg, Pd, Co, Ni, Cu, Zn, Hg, Er, Ti, Eu, Sn and Mn or represents two H atoms;
- $R_3$ and $R_5$ are each, independently, acetyl, vinyl, ethyl, 1-hydroxyethyl or an ether or ester of said 1-hydroxyethyl radical;
- $R_4$ is methyl or formyl;
- the dotted line at positions 7–8 represents an optional double bond; and
- $R_1$ and $R_2$ are identical, and are selected from the group consisting of:
  - (i) a $C_1$–$C_{25}$ hydrocarbyl radical that may be straight or branched, saturated or unsaturated, optionally substituted by one or more radicals selected from halogen, oxo (=O), OH, CHO, COOH, or $NH_2$, or interrupted by one or more heteroatoms selected from O, S and NH, or by carbocyclic or heterocyclic moieties;
  - (ii) a residue of an amino acid, an oligopeptide or a polypeptide containing a hydroxy group or of a derivative thereof selected from the group consisting of esters and N-protected derivatives, wherein said hydroxylated amino acid or derivative thereof is linked to the COO⁻residue of the Chl or BChl derivative through said hydroxy group;
  - (iii) a residue of a peptide as defined in (ii) linked to the COO⁻residue via a $C_1$–$C_{25}$ hydrocarbyl as defined in (i) wherein said $C_1$–$C_{25}$ saturated or unsaturated hydrocarbyl residue optionally substituted by one or more radicals selected from halogen, oxo (=O), OH, CHO, COOH, $NH_2$, or such a residue interrupted by one or more heteroatoms selected from O, S and NH, or by a phenyl ring is further substituted by an end functional group selected from OH, COOH, or $NH_2$;
  - (iv) a residue of a cell- or tissue-specific ligand selected from an oligo-peptide and a protein directly linked to the COO⁻ residue or via a $C_1$–$C_{25}$ hydrocarbyl as defined in (i) wherein said $C_1$–$C_{25}$ saturated or unsaturated hydrocarbyl residue optionally substituted by one or more radicals selected from halogen, oxo (=O), OH, CHO, COOH, $NH_2$ or such a reside interrupted by one or more heteroatoms selected from O, S, NH, or by a phenyl ring, is further substituted by an end functional group selected from OH, COOH, or $NH_2$; and
  - (v) a residue of a mono-, oligo- or polysaccharide or from a polyoxyethylene directly linked to the COO⁻ residue or via a $C_1$–$C_{25}$ hydrocarbyl as defined in (i) wherein said $C_1$–$C_{25}$ saturated or unsaturated hydrocarbyl residue optionally substituted by one or more radicals selected from halogen, oxo (=O), OH, CHO, COOH of $NH_2$, or such a residue interrupted by one or more heteroatoms selected from O, S and NH, or by a phenyl ring, is further substituted by an end functional group selected from OH, COOH, or $NH_2$;

comprising the reaction under anaerobic conditions of a (bacterio) chlorophyll, metal (bacterio) chlorophyll or (bacterio)pheophytin derivative carrying at position C-$13^2$ a $COOCH_3$ group and at position C-$17^2$ a $COOR_2$ group with an alcohol $R_1OH$, with the proviso that $R_1$ is not methyl, in the presence of tetraethyl-ortho-titanate, thus obtaining the desired C-$13^2$-$COOR_1$, C-$17^2$-$COOR_1$ diester and wherein the alcohol $R_1OH$ is used as the solvent.

11. A process according to claim 10, wherein M is a divalent metal selected from the group consisting of Mg, Pd, Co, Ni, Cu, Zn, Hg, Er, Ti, Eu, Sn, and Mn.

12. A process for the preparation of a chlorophyll compound according to claim 10, wherein $R_3$ is vinyl, $R_4$ is methyl or formyl, $R_5$ is ethyl and the dotted line at positions 7–8 represents a double bond.

13. A process for the preparation of a bacteriochlorophyll compound according to claim 10, wherein $R_3$ is acetyl, $R_4$ is methyl, $R_5$ is ethyl and the positions 7–8 are hydrogenated.

14. The process according to claim 13, wherein M is Mg, $R_1$ is propyl and $R_2$ is propyl.

15. The process according to claim 13, wherein, M is Pd, $R_1$ is tert-butylbenzyl and $R_2$ is tert-butylbenzyl.

16. The process according to claim 13, wherein M is Pd, $R_1$ is propyl and $R_2$ is propyl.

* * * * *